United States Patent [19]

Vail et al.

[11] Patent Number: 4,663,295
[45] Date of Patent: May 5, 1987

[54] ESTROGEN-PROGESTERONE CONTROL REAGENTS AND METHODS FOR MAKING SAME

[75] Inventors: Martha Vail, Huntington Beach; Robert E. Megraw, Tustin; Michael K. Hoskins, Irvine, all of Calif.

[73] Assignee: Ciba Corning Diagnostics Corp., Medfield, Mass.

[21] Appl. No.: 501,222

[22] Filed: Jun. 29, 1983

[51] Int. Cl.$^4$ .................... G01N 31/00; C12Q 1/00
[52] U.S. Cl. .................................. 436/18; 435/4
[58] Field of Search ............ 436/8, 18, 529, 15, 436/16; 435/4, 1, 240; 252/408.1, 358

[56] References Cited

U.S. PATENT DOCUMENTS

| | | | |
|---|---|---|---|
| 2,433,299 | 12/1947 | Seegers | 195/62 |
| 3,133,001 | 5/1964 | Muset | 195/68 |
| 3,413,198 | 11/1968 | Deutsch | 195/103.5 |
| 3,527,331 | 9/1970 | Deutsch | 195/103.5 |
| 3,753,925 | 8/1973 | Louderback | 252/408 |
| 3,962,037 | 6/1976 | Mitchell | 435/188 |
| 4,040,785 | 8/1977 | Kim et al. | 436/18 |
| 4,056,484 | 11/1977 | Heimburger et al. | 252/408 |
| 4,127,502 | 11/1978 | Limutti et al. | 252/408 |
| 4,216,117 | 8/1980 | Proksch et al. | 436/18 |
| 4,299,726 | 11/1981 | Crews et al. | 436/16 |
| 4,423,151 | 12/1983 | Baranczuk | 436/8 |
| 4,433,056 | 2/1984 | Baranczuk | 436/8 |

FOREIGN PATENT DOCUMENTS 0054096 6/1982 European Pat. Off. ............ 435/188

OTHER PUBLICATIONS

Proksch et al., "Preparation of Lyophilized Abnormal Hemoglobin Controls for a Cellulose Acetate Electrophoresis", Brief Scientific Reports, vol. 74, No. 1:64–67.
Bonderman et al., "Lyophilized Control for Determination of Glucose-6-Phosphate Dehydrogenase Activity in Homolysates", Clin. Chem., vol. 25, 5:815–816 (1979).
Bonderman et al., "A Lyophilized Hemoglobin Control Prepared from Stroma Free Homolysates", Clin. Chem. 26/2:305–308 (1980).

Primary Examiner—Deborah L. Kyle
Assistant Examiner—T. J. Wallen
Attorney, Agent, or Firm—Brian D. Voyce

[57] ABSTRACT

Reagents useful for steroid receptor assays containing both progesterone and estrogen receptors and methods. The reagents of the instant invention contain both estrogen and progesterone receptors in a stabilized format. A preferred embodiment includes target tissue material obtained from calf uteri having the required receptors, HEPES suspending buffer, a binding site activation inhibitor, dithiothreotol, plexiform stabilizing matrix means and an amount of inactive protein added as necessary to meet predetermined total protein levels.

14 Claims, No Drawings

ESTROGEN-PROGESTERONE CONTROL REAGENTS AND METHODS FOR MAKING SAME

FIELD OF THE INVENTION

This invention relates to reagents useful in clinical environments and more particularly to those useful in steroid receptor analysis.

BACKGROUND OF THE INVENTION

Steroid receptor analyses are performed in the clinical environment with increasing frequency due, at least, in part to the heightened awareness for the diagnostic value of the results. Specifically, it is now becoming generally accepted that an assessment of the presence of steroid receptors in biopsies of human breast carcinomas is essential to enable correct selection of hormone therapy. Although the mechanisms regarding interaction between receptors and therapy is as yet undetermined, it does seem clear that both estrogen and progesterone receptors may be utilized as predictive indices of a breast cancer patient's response to hormonal manipulation. Indeed, it is a commonly accepted principle that the presence of both receptors enhances the effectiveness of steroid therapy and makes such a route of treatment a viable alternative vis-a-vis chemotherapy or surgery. The chart presented below characterizes the present view regarding the presence or absence of estrogen receptors (ER) and/or progesterone receptors (PgR):

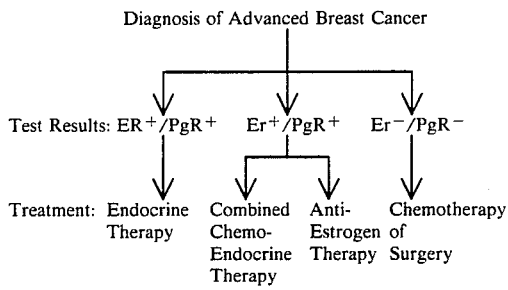

A general but informative discussion is provided by Wittliff, et al., Physiopathology of Endocrine Diseases and Mechanisms of Hormone Action, pages 397–411, 1981, Alan R. Liss, Inc., New York, New York, in a chapter entitled "Methods of Steroid Receptor Analyses and Their Quality Control in the Clinical Laboratory."

The progress in developing ER and PgR tests to clinical significance has been impeded by a variety of factors acting in concert. Foremost of those is the basic instability of steroid receptors due to their heat labile nature. This is of particular concern with control reagents necessary for comparison with any tissue biopsy. Consequently, the conventional art has sought a variety of mechanisms in an attempt to ammeliorate the stability problem.

Relatively early it was discovered that the progesterone and estrogen receptors were relatively stable while in the form of tissue preparations, particularly when such preparations were lyophilized and kept frozen. See for instance Koenders, et al., "Influence of Lyophilization and Subsequent Storage of Target Tissue on Steroid Receptors, Steroid Receptors and Hormone-Dependent Neoplasia" edited by Wittliff, Masson Publishing, New York, N.Y. Such a solid tissue control material is comparable to patient biopsy tissue and accordingly must be treated in like fashion. Some investigators advocate the tissue control's merit as providing a control for the homogenization aspects of the assay procedure. To date, only one tissue control material has been available (from New England Nuclear under the tradename Rianen Assay System) and it has failed to relieve the existing interlaboratory confusion resulting from the plethora of distinguishable techniques and methods being practiced. As expected, this nonuniformity of procedures effectively prohibits useful correlation of interlaboratory results.

The lack of common procedures has been further exacerbated because some investigators have sought to maintain a single laboratory control by making their own progesterone or estrogen receptor controls, typically from rat uteri. As may be expected, clinical environments do not lend themselves to the efficient production of controls, especially since production of these materials is a difficult, time consuming and complex matter. Devotion of valuable resources to the production of controls not only reduces the clinical laboratory's effectiveness, but also introduces significant sources of error further limiting the ability to compare results from different laboratories.

It is an object of the present invention to provide a control material possessing both estrogen and progesterone receptors which may be commonly used by laboratories as a control reagent thereby instituting a standard permitting the comparison of laboratory results.

Materials previously employed to provide estrogen receptors include human breast tumor and calf uterus tissue. It has been reported that when such tissue is lyophilized and kept at 0°–4° C., there may be no loss of estrogen binding sites for up to two years. See Benraad, et al., "Estradiol Receptor Activity in Lyophilized Calf Uterus and Human Breast Tumor Tissue", Cancer 46:2762–2764, 1980. It may be noted, however, that the material described by Benraad provides only estrogen binding receptor sites and makes no mention of progesterone binding sites. Progesterone sites have been traditionally characterized as even more unstable than estrogen sites thus greatly increasing the difficulty of providing a stable reagent material having both types of binding sites.

It is another object of the present invention to overcome these problems by providing a material having both progesterone and estrogen receptors in a form having the stability necessary for acceptance in the clinical environment.

Still other sources may be used to provide receptor binding sites. See for instance Korenman, "Radio-Ligand Binding Assay of Specific Estrogens Using a Soluble Uterine Macromolecule", J.Clin.End. and Med. 28:127–130, 1968 which describes the use of uteri from pregnant rats. Bojar, et al., "Investigation of the Thermostability of Steroid Hormone Receptors in Lyophilized Calf Uterine Tissue Powder", Cancer 46:2770–2774, 1980 provides discussion with respect to calf uterine tissue.

The actual structure of the receptors is still a subject for investigation and some recent theories are described by Wittliff in "Steroid Receptor Interactions in Human Breast Carcinoma", Cancer 46,12:2953–2960 (1980). Additional experimental results describing the ability of vanadate and sodium molybdate to inhibit the receptor activation process and thus preserve receptor activity necessary for subsequent assay testing, have been reported in a series of articles: Nishigori, et al., "Inhibition of Progesterone Receptor Activation by Vanadate," archives of Biochem and Biophysics, Volume 203, 2:600–604, 1980; Anderson, et al., "Sodium Molybdate Increases the Amount of Progesterone and Estrogen Receptor Detected in Certain Human Breast Cancer Cytosols," Steroids Volume 35, 3:273–280, 1980; and Maki, et al., "Alterations in Glucocorticoid Receptor Conformation by Molybdate," J. Biochem. 87, 6:1851–1854 (1980).

As has been previously mentioned, investigators in this field have searched for a useful, stabilized cytosol control preparation. Stabilized as used herein means there should be a recovery of at least 90% of the original receptor activity following storage. A cytosol type of preparation, as opposed to the well-known powders heretofore generally available, constitutes tissue which has been homogenized and centrifuged to form a cell-free solution. Although cytosol solutions may be readily prepared, heretofore, none of these cytosol solutions contained both progesterone and estrogen receptors in a stabilized format. For instance, the cytosol preparation described by Vermousek, et al., in "Stable Standard for Determination of Oestrogen Receptor," J.Clin.Chem.-Biochem 19:865, 1981, failed to provide more than 20% of the original binding capacity following lyophilization.

It is another object of the instant invention to provide a cytosol preparation suitable for lyophilization and storage in that form for at least a year which, upon reconstitution, provides at least 90% of the original receptor activity, said receptors including both estrogen and progesterone receptors.

The inability of conventional methods to provide such a preparation is further exemplified in an article by Koenders, et al., "Preparation of Lyophilized Reference Samples for Quality Control of Steroid Receptor Measurements," The Ligand Review 3:22–39, 1981. That article describes the stability of lyophilized *tissues* with respect to estrogen and progesterone receptor activities and at 4° storage, good activity was reported after 14 months. Compare this however to the reported lyophilized *cytosol* of pig and calf uterine tissues during storage over a similar period of time. As expected, the more hardy ER binding sites remained relatively unchanged; however, PgR activity became virtually nonexistent after only one and a half months of lyophilization storage. Indeed, even lyophilized human breast tumor tissue showed significant decreases in activity after only a few months' storage.

It is yet a further object of the present invention to provide stabilization methods and preparations to permit stabilized storage of calf uterine cystols having both ER/PR binding sites.

SUMMARY OF THE INVENTION

In accordance with the objects of the present invention, there are provided stabilized reagents containing both estrogen receptors and progesterone receptors comprising processed tissue having both estrogen and progesterone receptors associated therewith, a suspending buffer which in the preferred embodiment is HEPES, sodium molybdate or vanadate as a binding site protector, dithiothreitol, additional protein in an inactive form, bovine serum albumin in a preferred embodiment, added in order to insure the final reagent meets a predetermined total protein level and, plexiform stabilizing means for stabilizing and protecting the reagent during storage. This plexiform stabilizing means provides necessary protection during lyophilization by functioning as a cryoprotective agent.

Indeed it has been surprisingly found by the inventors hereof that estrogen and progesterone receptor containing materials may be stabilized, contrary to prior beliefs, for extended periods of time particularly in a lyophilized format. The methods for such preservation include the addition of both a binding site activation inhibitor and the plexiform stabilizing means, advantageously chosen to be sodium molybdate and the reducing sugar lactose, respectively.

DETAILED DESCRIPTION OF THE INVENTION AND MOST PREFERRED EMBODIMENTS

A variety of target tissues containing both progesterone and estrogen receptors may be employed and include for instance animal tissues such as rat mammary glands, pig uteri and human tissues such as human breast material. The inventors hereof however have found that calf uteri, and in particular, the uterine endometrium, to be the most preferred material with which to work. This material does, however, require special handling. Ideally, the uterus should be obtained from a born calf, have a weight of approximately 30–50 grams, and be devoid of blood and connective tissue. After removal from the calf, the tissue is advantageously frozen at $-80°$ C. and subsequently processed under nitrogen. This includes breaking up the tissue into roughly one inch size pieces followed by grinding and pulverizing to obtain a fine powder. Thereafter the material is homogenized by either grinding or sonicating, processes well known, and the resultant material ultracentrifuged to remove cellular debris. The supernatant is the cytosol fraction which is thereafter ideally diluted or otherwise adjusted to obtain the 2–4 milligram per ml protein levels desired in a final reagent. The protein level may be typically measured using well known standard protein assay methods. If necessary, protein such as Bovine Serum Albumin or preferably non-specific cellular protein such as globulin or the cytosol from mature bovine uteri may be added to obtain the required total protein levels.

The thusly processed material may be tested to determine the estrogen and progesterone binding capacity by employing a radiolabeled estrogen and progesterone such as that provided under the New England Nuclear Rainen trademark. Typically, six different concentrations of this radiolabelled material are utilized in the assay in conjunction with a nonspecific binding control for each concentration. The results are plotted and the x-intercept determined. Although the values (x-intercept) calculated cannot be classified on an absolute basis, due largely to the heretofore great variation between laboratory results, it is generally understood that ER in the range of 100 fmole ($10^{-15}$) per milligram of cytosol protein is interpreted as positive with the border line or gray zone ranges identified as 5–20 with 30+fmole/mg identified as strongly suspicious. The progesterone receptor values run somewhat higher. 150 fmole/mg cytosol protein is understood to represent a positive result with the positive "gray zone" occurring at approximately 5–30 fmoles/mg cytosol protein.

The target tissue is preferably homogenized with a buffer such as TRIS or HEPES although the other "GOODS" buffer (see p. 396 of the Feb. 1983 SIGMA CATALOG) such as MOPS, MES, PIPES, etc. may be substituted therefor. Each of these buffers may be used at a 10 mmole/1 concentration with a final concentration at reconstitution ideally chosen to be in the range of about 0.025 molar to about 0.15 molar; the most preferred concentration being 50 mmolar. The most preferred embodiment comprises HEPES buffer as the inventors hereof have discovered the TRIS buffer has minimal buffering capacity at the preferred pH value of about 7.4 at the standard storage temperature of 4° C. It may be readily appreciated, however, that other buffers may be employed in substitution.

The preferred embodiment includes dithiothreotol in a final concentration in the range of 0.5–2 mmolar. It is believed that dithiothreotol protects the receptor sulfhydryl groups although the inventors hereof do not wish to be held to this theory. The preferred final concentration of this reagent otherwise known as Clelands reagent, should be in the range of approximately 1 mmole. Alternately, active sulfhydryl compounds such as monothioglycerol, dithioerythreitol, n-acetyl cystene, B-mercapto ethanol and the like may be substituted for dithiothreitol.

An important ingredient in the invention hereof is the addition of a binding site activation inhibitor such as sodium molybdate or vanadate. It is preferred that the inhibitor be provided in the range of approximately 1–5 mmolar final concentration, with the most preferred embodiment utilizing this reagent in a final concentration of about 2.5 mmolar. It is important to note that the amounts employed herein are significantly less than those employed by conventional techniques (10–20 mmole). The inventors hereof have discovered that the greater concentration ranges of the prior art interfere with the WADDELL type protein assays; an assay commonly employed by many researchers. As has been previously intimated, the mechanisms by which the activation inhibitors protect the binding sites is still relatively unknown.

All embodiments of the ER/PgR reagents contain an effective amount of a plexiform stabilizing means. The effective amount is that required to obtain significantly greater stability of the extrogen and progesterone receptors and is ideally in the range of 0–0.05–0.4 final molar concentration. The inventors hereof have found reducing sugars to be the preferred plexiform stabilizing means as it is believed they serve to provide a 3 dimensional network for holding the binding site molecules and thereby protecting them from oxidation and stabilizing them during the various phases of lyophilization. These and related aspects are more fully described in an application entitled "Stabilized Multi-Parameter Control Product" by Hoskins, filed concurrently herewith and fully incorporated herein by reference. The most preferred embodiments employ either sucrose, glucose, lactose or combinations thereof. Lactose is the most preferred. The ideal final concentration is approximately 75 mmolar.

The most preferred embodiment of the reagent will be lyophilized and will also include EDTA as a preservative preferably in a final concentration of approximately 0.1 mmolar. Such a preservative acts to inhibit microbial contamination; however, its absence results in no significant ER/PR assay differences. Other non-interfering preservatives may be employed in substitution.

It will be readily appreciated by those skilled in the art that various substitutions and alterations of the above including variations of the preferred concentration ranges as well as substitutions for the described components may be made without deviation from the spirit and principles of the instant invention.

We claim:

1. A stabilized estrogen receptor-progesterone receptor reagent comprising:
   (a) processed tissue having estrogen and progesterone receptors;
   (b) a suspending buffer selected from the group consisting of "GOODS" buffers;
   (c) an effective amount of binding site projector selected from the group consisting of sodium molybdate and sodium vanadate;
   (d) an active sulfhydryl compound;
   (e) an amount of inactive protein added as necessary to insure the final reagent contains a desired total mg protein per ml level; and
   (f) a reducing sugar.

2. The reagent provided for in claim 1 wherein the suspending buffer is HEPES buffer, the inactive protein is mature bovine uterine cytosol, the plexiform stabilizing means is selected from the group consisting of glucose, sucrose, lactose, and combinations thereof; and the active sulfhydryl compound is dithrothreitol.

3. The reagent as provided for in claim 2 wherein the plexiform stabilizing means is lactose, the binding site protector is sodium molybdate and the processed tissue is calf uterine endometrium.

4. The reagent as provided for in claim 3 wherein the preservative means is EDTA present in a final concentration in a range of approximately 0.1–1.5 mmolar.

5. The reagent as provided for in claim 4 in lyophilized form.

6. The reagent as provided for in claim 3 in lyophilized form.

7. The reagent provided for in claim 2 wherein the final reagent has a total protein level in the range of approximately 2–4 milligrams per ml, HEPES is present in the final concentration in the range of about 0.025 molar to about 0.15 molar, the binding site protector is present in a final concentration in the range of about 1–5 mmolar, dithiothreotol is present in the final concentration in the range of about 0.5–2 mmolar and the plexiform stabilizing means is a reducing sugar or sucrose present in a final concentration in the range of about 0.05–0.4 molar.

8. The reagent as provided for in claim 7 wherein the binding site protector is sodium molybdate and the plexiform stabilizing means is lactose.

9. The reagent as provided for in claim 8 wherein sodium molybdate is present in the final concentration of about 2.5 mmole, the plexiform stabilizing means is present in a final concentration of about 75 mmolar, the HEPES buffer is present in a final concentration of approximately 50 mmole, and dithiothreotol is present in a final concentration of approximately 1 mmolar.

10. The reagent as provided for in claim 9 further comprising EDTA in a final concentration of approximately 0.2 mmole.

11. The reagent as provided for in claim 10 in lyophilized form.

12. The reagent as provided for in claim 8 in lyophilized form.

13. The reagent as provided for in claim 9 in lyophilized form.

14. The reagent as provided for in claim 1 in lyophilized form.

* * * * *